United States Patent
Kilgard et al.

(10) Patent No.: US 6,221,908 B1
(45) Date of Patent: Apr. 24, 2001

(54) SYSTEM FOR STIMULATING BRAIN PLASTICITY

(75) Inventors: Michael P. Kilgard, Richardson, TX (US); Michael M. Merzenich, San Francisco, CA (US)

(73) Assignees: Scientific Learning Corporation, Berkeley; Regents of the University of California, Oakland, both of CA (US)

( * ) Notice: Subject to any disclaimer, the term of this patent is extended or adjusted under 35 U.S.C. 154(b) by 0 days.

(21) Appl. No.: 09/224,510

(22) Filed: Dec. 31, 1998

Related U.S. Application Data

(60) Provisional application No. 60/077,818, filed on Mar. 12, 1998.

(51) Int. Cl.[7] .............................. A61K 31/22; A61K 1/18
(52) U.S. Cl. .............................. 514/546; 514/642; 607/2; 607/3; 607/45
(58) Field of Search .................................... 514/546, 642; 607/3, 2, 45

(56) References Cited

U.S. PATENT DOCUMENTS 5,601,835  2/1997  Sabel et al. .......................... 424/424

OTHER PUBLICATIONS

Hasselmo, M.E., "Neuromodulation and Cortical Function: Modeling the Physiological Basis of Behavior," *Behavioural Brain Research*, 67:1–27, 1995.

Juliano, S.L., et al., "Cholinergic Depletion Prevents Expansion of Topographic Maps in Somatosensory Cortex," *Proc. Natl. Acad. Sci. USA*, 88:780–784, Feb. 1991.

Winkler, J., et al., "Essential Role of Neocortical Acetylcholine in Spatial Memory," *Nature*, 375:484–487, Jun. 8, 1995.

Baskerville, K.A., et al., "Effects of Cholinergic Depletion on Experience–Dependent Plasticity in the Cortex of the Rat," *Neuroscience*, vol. 80, No. 4, pp. 1159–1169, 1997.

Rasmusson, D.D., et al., Frequency–Dependent Increase in Cortical Acetylcholine Release Evoked by Stimulation of the Nucleus Basalis Magnocellulars in the Rats, *Brain Research*, 594:150–154, 1992.

Bakin, J.S., et al., "Induction of Physiological Memory in the Cerebral Cortex by Stimulation of the Nucleus Basalis," *Proc. Natl. Acad. Sci. USA*, 93:11219–11224, Oct. 1996.

Metherate, R., et al., Pasal Forebrain Stimulation Modifies Auditory Cortex Responsiveness by an Action at Muscarinic Receptors, *Brain Research*, 559:163–167, 1991.

Richardson, R.T., et al., "Electrophysiological Studies of the Functions of the Nucleus Basalis in Primates," *The Basal Forebrain*, 1991.

*Primary Examiner*—Kathleen K. Fonda
(74) *Attorney, Agent, or Firm*—Christensen O'Connor Johnson & Kindness PLLC

(57) ABSTRACT

A system for stimulating brain plasticity releases acetylcholine into the learner's brain while the learner is receiving incoming stimuli or performing an activity during the learning process. It is believed that acetylcholine helps the brain in the learning and memorizing process. In one embodiment, the nucleus basalis region of the learner's brain is electrically stimulated to release acetylcholine, thereby aiding the learning and memorizing process. The electrical stimulation advantageously reduces the need for the learner to attach "behavioral importance" and to pay close attention on the incoming stimuli or activity to stimulate the release of acetylcholine. In other embodiments, delivery systems such as microinjection, implanted micro release devices or implanted photo-sensitive release devices may be used to release acetylcholine into the brain to aid the learning process.

8 Claims, No Drawings

SYSTEM FOR STIMULATING BRAIN PLASTICITY

This application claims priority from U.S. Provisional Application No. 60/077,818, filed Mar. 12, 1998.

This invention was supported in part by grant numbers: National Institutes of Health grant NS-10414; ONR grant N00014-96-102. The government has certain rights in the invention.

FIELD OF THE INVENTION

The present invention relates to learning systems and, more particularly, to learning systems directed toward improving the ability of a learner's brain to make new networks of nerve connections.

BACKGROUND

Little is known about the mechanisms that allow the brain (i.e., the cortex) to selectively improve the neural representations of behaviorally important stimuli while ignoring irrelevant stimuli. Some current neuroscience research indicates that learning is related to the ability of the brain to form new networks of nerve connections, a phenomenon termed herein as "brain plasticity". The formation of new nerve connections is also referred to herein as brain reorganization. Diffuse neuromodulatory systems may facilitate cortical plasticity by acting as a teacher to mark important stimuli. That is, it is believed that learning may be related to many factors such as, for example, the "behavioral importance" collectively attached by several brain regions in weighing or processing the subject matter to be learned (i.e., the incoming stimuli or activity). In addition, it is believed that learning is also related to how much attention the learner focuses on the incoming stimuli. Thus, it is believed that learners generally must put significant effort into learning and memorizing processes. It is believed that some types of learning disability may be related to an impaired ability to focus attention and/or attach behavioral importance on the incoming stimuli or activity.

The learning and memorizing process can be further affected by injury to the brain caused, for example, by a stroke. Stroke patients often incur lost brain functions such as speech, accurate hearing and movement. However, it has been observed that stroke patients often lack the will to participate vigorously in rehabilitation programs for recovering or relearning brain functions lost due to the stroke. Further, because the stroke damages brain cells, brain resources are more limited or may even have a diminished ability to generate "behavioral importance", which may contribute to the commonly slow recovery process.

Accordingly, there is a need for a learning system that stimulates brain plasticity with reduced dependence on both behavior importance and the degree of attention on the incoming stimuli.

SUMMARY

In accordance with the present invention, a system for stimulating brain plasticity is provided. In one aspect of the present invention, acetylcholine is released into the learner's brain during the learning process. It is believed that acetylcholine helps the brain in the learning and memorizing process. The greater the release of acetylcholine, the faster and stronger the learning and memory. In addition, it is thought that the nucleus basalis region of the brain releases acetylcholine as a function of the amount of attention paid by the learner and also the degree of "behavioral importance" generated in response to the incoming stimuli. In one embodiment of the present invention, the learners nucleus basalis is electrically stimulated to increase the release of acetylcholine, thereby aiding the learning and memorizing process. The electrical stimulation advantageously reduces the need for the learner to attach "behavioral importance" and to pay close attention on the incoming stimuli or activity to stimulate the release of acetylcholine. In other embodiments, delivery systems such as microinjection, implanted micro release devices or implanted photo-sensitive release devices may be used to release acetylcholine into the brain to aid the learning process.

Thus, in one embodiment, the present invention provides a method of stimulating brain plasticity that includes the steps of providing acetylcholine in a subject's brain and providing stimulus to the subject substantially coincident with the provision of acetylcholine. In a preferred embodiment electrical stimulation of the subject's nucleus basalis is used to release acetylcholine into the subject's brain. Alternatively, or in addition to electrical stimulation of the subject's nucleus basalis, acetylcholine is released into an artery feeding the subject's brain by a variety of means including microinjection or through a device implanted in the subject's body that time-releases acetylcholine.

In another embodiment, the present invention provides a method of stimulating brain plasticity that includes the step of electrically stimulating the nucleus basalis of a subject's brain. The electrical stimulation of the nucleus basalis of a subject's brain can be in the form of multiple electrical stimuli. In a preferred embodiment, the electrical stimulation of the subject's nucleus basalis is accompanied by a behaviorally important stimulus. Examples of behaviorally important stimuli include the provision of information that is to be learned, for example auditory or visual information whereby the subject learns to read, speak or ambulate after brain damage.

DETAILED DESCRIPTION

Embodiments of a system for stimulating brain plasticity according to the present invention were developed from an animal study and adapted to human. More specifically, to explore and map out in detail the learning-related changes in the auditory cortex, normal rats were exposed to sounds of assorted frequencies and bandwidths about three hundred times per day for about twenty days. The experimental group of rats received auditory stimuli coinciding with mild electrical stimulation of the nucleus basalis. Another group of rats received the auditory stimuli but no electrical stimulation. In the electrically stimulated rats, the auditory cortex became dramatically rearranged to respond to the specific frequencies used as sound stimuli. No changes were recorded in rats in which the nucleus basalis was not stimulated.

Brains of humans and other mammalian species have been trained to distinguish sound frequencies with parallel brain plasticity, but the extent of reorganization generated by activating the nucleus basalis is substantially larger than the reorganization that is typically observed after several months of intensive behavioral training. To better understand the invention, the study is described in more detail below. Note that bracketed citations to other references are provided in the description. These cited references are incorporated herein by reference in their entireties.

The study demonstrates that episodic, electrical stimulation of nucleus basalis paired with an auditory stimulus results in a massive progressive reorganization of the primary auditory cortex in the adult rat. This simple paradigm causes receptive field sizes to be narrowed, broadened, or left unaltered depending on specific parameters of the acoustic stimulus paired with nucleus basalis activation. This differential plasticity parallels the receptive field remodeling that results from different types of behavioral training, suggesting that input characteristics may be able to drive appropriate receptive field alterations independent of explicit knowledge of the task. These findings suggest that the basal forebrain plays an active instructional role in representational plasticity.

The mammalian cerebral cortex is a highly sophisticated self-organizing system [Singer, W., *Eur. Arch. Psych. Neurol. Sci.* 236: 4–9 (1986)]. The statistics of sensory inputs from the external world are not sufficient to guide cortical self-organization because the behavioral importance of inputs is not strongly correlated with their frequency of occurrence. The behavioral value of stimuli has been shown to regulate learning in experiments conducted over more than a century [Thorndike, E. L. *Animal Intelligence*, Macmillan, New York 1911]. Recently, behavioral relevance has been shown to directly modulate representational plasticity in cortical learning models [E. Ahissar et al., Science 257: 1412 (1992); N. M Weinberger *Curr. Opin. Neurobiol.* 3: 570 (1993); E. Ahissar, & M. Ahissar *Curr. Opin. Neurobiol.*, 4: 80 (1994); M. M. Merzenich, G. H. Recanzone, W. M. Jenkins, K. A. Grajski, *Cold Spring Harb. Symp. Quant. Biol.* 55: 873 (1990)]. The cholinergic nucleus basalis (NB) has been implicated in this modulation of learning and memory. The NB is uniquely positioned to provide the cortex with information about the behavioral importance of particular stimuli, because it receives inputs from limbic and paralimbic structures and sends projections to the entire cortex [M. M. Mesulam, E. J. Mufson, B. H. Wainer, A. I. Levey *Neuroscience* 10: 1185 (1983); D. B. Rye, B. I. Wainer, M. M. Mesulam, E. J. Mufson, C. B. Saper, *Neuroscience* 13: 627 (1984); M. Steriade and D. Biesold, *Brain Cholinergic Systems* (Oxford University Press, New York 1990)]. Consistent with this notion, NB neurons are activated as a function of the behavioral significance of stimuli [R. T. Richardson and M. R. DeLong, *Activation to acquisition. Functional aspects of the basal forebrain cholinergic system* (Birkhauser, Boston, 1991), pp. 135–166; R. T. Richardson and M. R. DeLong, *Adv. Exp. Med. Biol.* 295: 233 (1991); A. E. Butt, G. Testylier, R. W. Dykes, *Psychobiol.*, 25: 18 (1997)]. Several forms of learning and memory are impaired by cholinergic antagonists and by NB lesions [R. C. Peterson, *Psychopharmacol.* 52: 283 (1977); H. H. Webster, U Hanisch, R. W. Dykes, & D. Biesold, *Somatosens. Mot. Res.* 8: 327 (1991); A. E. Butt and G. K. Hodge, *Behav. Neurosci.* 109: 699 (1995); G. Leanza, J. Muir, O. G. Nilsson, R. G. Wiley, S. B. Dunnet, A. Bjorklund, *Eur. J. Neurosci.* 8: 1535 (1996); K. A. Baskerville, J. B. Schweitzer, P. Herron, *Neuroscience* 80: 1159 (1997)]. Even the highly robust cortical map reorganization that follows peripheral dennervation is blocked by NB lesions.

Many studies using acute preparations have shown that electrical stimulation of the NB [R. Metherate and J. Ashe, *Brain Res.* 559: 163 (1991); R. Metherate and J. H. Ashe, *Synapse* 14: 132 (1993); J. M. Edeline, C. Maho, B. Hars, E. Hennevin, *Brain Res.* 636: 333 (1994); J. M. Edeline, B. Hars, C. Maho, E. Hennevin, *Exp. Brain Res.* 97: 373 (1994)] or local administration of acetylcholine (ACh) [R. Metherate, N. Tremblay, R. W. Dykes, *J. Neurophysiol.*, 59: 1231 (1988); T. M. McKenna, J. H. Ashe, N. M. Weinberger, *Synapse* 4: 30 (1989); R. Metherate and N. M. Weinberger, *Brain Res.* 480: 372 (1989); R. Metherate and N. M. Weinberger, *Synapse* 6: 133 (1990)], can modulate stimulus-evoked single-unit responses. The variability across studies in the direction, magnitude, and duration of the modulation in response to ACh has made it difficult to relate these effects to long-term cortical map plasticity. Although studies using stimulation of NB reported mostly facilitation of the response to the paired stimulus, in several studies using local administration of ACh to alter receptive field organization the opposite effect was reported. In these studies, ACh most often caused a significant stimulus-specific decrease in cortical responsiveness following the pairing procedure. The average duration of the plasticity also varied across studies from less than ten minutes to more than an hour.

The following examples merely illustrate the best mode now contemplated for practicing the invention, but should not be construed to limit the invention.

EXAMPLE 1

The Role of the Nucleus Basalis (NB) In Representational Plasticity

To clarify the role of NB in representational plasticity, we investigated the consequences of the long-term pairing of tones with episodic NB stimulation. A chronic stimulating electrode was implanted in the right NB of twenty-one adult rats. Platinum bipolar stimulating electrodes were lowered 7 mm below the cortical surface 3.3 mm lateral and 2.3 mm posterior to bregma in ~300 g barbiturate anesthetized rats, and cemented into place using sterile techniques approved under UCSF animal care protocols. After two weeks of recovery, 250 ms (or a 15 Hz train of six 25 msec) 50 dB SPL tones were paired with 200 ms of NB electrical stimulation in a sound-shielded, calibrated test chamber (five days/week). Electrical stimulation began either 50 ms after tone onset (n=15) or 200 ms before (n=6). The two timings did not appear to affect plasticity and data from both groups were pooled. The current level (70–150 $\mu$Amp) was chosen to be the minimum necessary to desynchronize the EEG during slow wave sleep for 1–2 seconds. Stimulation consisted of 100 Hz capacitatively coupled biphasic pulses of 0.1 ms duration. Tonal and electrical stimuli did not evoke any observable behavioral responses (i.e., did not cause rats to stop grooming or if sleeping, awaken). The tone paired with NB stimulation occurred randomly every 8–40 seconds. Pairing was repeated three to five hundred times per day for 20–25 days. The rats were unanesthetized and unrestrained throughout this procedure.

Twenty-four hours after the last session, each animal was anesthetized and a detailed map of primary auditory cortex (A1) was generated from 70–110 microelectrode penetrations. Twenty-four hours after the last pairing, animals were anaesthetized with pentobarbital and the right auditory cortex surgically exposed. Parylene-coated tungsten microelectrodes (2 M$\Omega$) were lowered 550 $\mu$m below the pial surface (layer 4/5), and complete tuning curves were generated with 50 ms pure tones (with 3 ms ramps) presented at 2 Hz to the contralateral ear. The evoked spikes of a small cluster of neurons were collected at each site. To determine the effects of conditioning on the bandwidth of individual neurons, spike waveforms were collected during eight experiments and sorted off-line using software from Brainwave Technologies. Penetration locations were referenced using the cortical vasculature as landmarks. Primary auditory cortex was defined on the basis of its short latency (9–20 msec) responses and continuous tonotopy (BF increases from posterior to anterior). Responsive sites that exhibited clearly discontinuous best frequencies and either long latency responses, unusually high threshold, or very broad tuning were considered to be non-A1 sites. Penetration sites were chosen to avoid blood vessels while generating a detailed and evenly spaced map. The edges of the map were estimated using a line connecting the nonresponsive and non-A1 sites. Effect of conditioning on mean bandwidths across all conditions was determined using ANOVA; pairwise comparisons were analyzed by Bonferroni post-hoc tests. During this cortical mapping phase, experimenters were blind to the tone frequency that had been paired with NB stimulation. Frequency-intensity response characteristics of sampled neurons were documented in every penetration by presenting 45 pure tone frequencies at 15 sound intensities. Tuning curves were defined by a blind, experienced observer. The set of tone frequencies presented at each site was approximately centered on the BF of each site. Thus, during analysis each tuning curve is approximately centered in the stimulus space and simply blanking the axes and analyzing the sites in random order allowed for tuning curve characterization to be completely blind. Using custom analysis software, the tuning curve edges for each site were defined and recorded without the possibility of experimenter bias.

In naive rats, BFs were evenly distributed across the entire hearing range of the rat, in accordance with the well-known tonotopic organization of A1 [S. L. Sally and J. B. Kelly, *J. Neurophys.* 59: 1627 (1988)].

Pairing a specific tonal stimulus with NB stimulation resulted in remodeling of cortical area A1 in all twenty-one experimental rats. A 50 dB 9 kHz tone was paired with NB stimulation approximately 300 times per day over a period of 20 days. This paradigm produced a clear expansion of the region of cortex that represented frequencies near 9 kHz. After pairing, neurons from 20 penetrations into a conditioned neural map had BFs within a third of an octave of 9 kHz, compared to only six in the equivalently sampled control map. The increase in 9 kHz representation resulted in a clear decrease in the area of A1 that responded to lower frequencies. In the control map, 22 penetrations had BFs less than 5 kHz, compared to only four penetrations in the conditioned map. It should be noted that the decrease in low frequency responses is not a consistent finding. In other examples the low frequency responses appeared unaltered and the representation of higher frequencies was decreased.

Because the tone paired with NB stimulation was well above threshold, it was important to examine not only the shifts in the tuning curve tips, but also the responses of cortical neurons to tones at the conditioned intensity. During pairing, many of the neurons with BFs different from 9 kHz were excited by the auditory stimulus because most rat A1 tuning curves broaden as intensity is increased. In the naive map, less than 25% of neurons within A1 responded to 9 kHz presented at 50 dB. By contrast, almost 50% of the conditioned cortex responded to the same stimulus.

The cortical area representing the paired stimulus nearly doubled in ten animals in which a frequency of 4, 9, or 19 kHz tones was paired with the NB stimulation. These results indicate that the responses of tens or hundreds of thousands of A1 neurons can be altered by pairing tones with NB stimulation in a passively stimulated animal.

In four animals, NB stimulation was paired with a train of six 9 kHz tones pips (25 msec) presented at 15 Hz to test the effects of increasing temporal structure in the auditory stimulus. Conditioning with this stimulus unexpectedly resulted in even greater cortical reorganization than conditioning with a 250 ms tone ($p<0.01$). The 9 kHz isofrequency band is increased from roughly 250 $\mu$m wide in a naive A1 to more than a millimeter wide. After pairing, over 85% of A1 responded to 9 kHz at 50 dB. Additionally, 50% of A1 penetrations had best frequencies within one-third of an octave of 9 kHz, compared to less than 15% in the control animals. It should be noted that the extent of cortical map reorganization generated using NB activation is significantly larger than the reorganization typically observed after several months of operant training [G. H. Recanzone, C. E. Schreiner, M. M. Merzenich, *J. Neurosci.* 13: 87 (1993); W. M. Jenkins, M. M. Merzenich, M. T. Ochs, T. Allard, E. Guic-Robles, *J. Neurohysiol.* 63: 82 (1990); G. H. Recanzone, M. M. Mcrzenich, W. M. Jenkins, K. A. Grajski, H. R. Dinse, *J. Neurophysiol.* 67: 1031 (1992)].

The six short tones presented at 15 Hz evoked less than 30% more spikes than a single tone, because most rat A1 neurons do not follow onsets presented faster than 12–14 Hz. It seems unlikely that the larger reorganization evoked with stimulus trains is simply due to an increased cortical response to the stimuli.

Two animals were mapped after only one week of conditioning with the 15 Hz stimulus to examine the rate of cortical remodeling evoked by our paradigm. The 9 kHz representation was increased by 18% after one week of training. This reorganization was nearly halfway to the 44% increase that was recorded following a month of conditioning, indicating that the cortical remodeling generated by NB stimulation was progressive in nature.

To probe the competitive processes underlying cortical reorganization, five rats were conditioned with two different randomly interleaved tones that were over an octave apart. Two distinct classes of reorganizations resulted. The tuning curve tips were either (1) shifted toward a point between the two conditioned frequencies, so that both were within the receptive field at 50 dB (n=3); or (2) shifted toward only one of the two conditioned frequencies (n=2). The two classes of results may be the consequence of subtle variations in A1 prior to NB pairing, which can have large effects when competitive processes are involved.

To document that NB activation is required for the cortical reorganizations observed in this study, during four of our experiments two additional frequencies were delivered on identical presentation schedules as the paired tones, but were not paired with NB stimulation. These stimuli, which never occurred within eight seconds of NB stimulation, did not measurably affect cortical responses or representations. In contrast to the large changes induced by pairing tones with NB stimulation, no significant cortical map reorganizations were observed in previous experiments after tens of thousands of behaviorally irrelevant stimuli were presented over three to five months [S. L. Sally and J. B. Kelly, *J. Neurophys.* 59: 1627 (1988); W. M. Jenkins, M. M. Merzenich, M. T. Ochs, T. Allard, E. Guic-Robles, *J. Neurohysiol.* 63: 82 (1990)]. Additionally, short-term repetition of one frequency without behavioral relevance (habituation) results in a dramatic decrease in A1 responses to that frequency [C. D. Condon and N. M. Weinberger, *Behav. Neurosci.* 105, 416 (1991)]. These studies suggest that stimulus presentation without behavioral importance does not result in significant map changes. Although unlikely to be a contributing factor, it is acknowledged that animals that experienced extensive stimulus presentation without any NB stimulation were not studied.

Microdialysis experiments have shown that electrical stimulation of the NB results in ACh release in the cortex [F.

Casamenti, G. Deffenu, A. L. Abbamondi, G. Pepeu, *Brain Res. Bull*. 16: 689 (1986); D. D. Rasmusson, K. Clow, J. C. Szerb, *Brain Res*. 594: 150 (1992); M. E. Jimenez-Capdeville, R. W. Dykes, & A. A. Myasnikov, *J. Comp. Neurol*. 381: 53 (1997)]. Additionally, both the short-term plasticity and EEG desynclronization evoked by NB stimulation are blocked by atropine [B. Hars, C. Maho, J. M. Edeline, E. Hennevin, *Neuroscience* 56: 61 (1993); J. S. Bakin, and N. M. Weinberger, *Proc. Natl. Acad. Sci. USA* 93: 11219 (1996)]. Thus, the cortical plasticity demonstrated in this report likely involves the release of cortical ACh paired with tones. To test for the necessity of ACh release in our paradigm, 19 kHz was paired with electrical stimulation of the NB in animals with highly specific lesions of the cholinergic NB neurons. No significant increase in the 19 kHz representation was observed in lesioned animals. The cholinergic neurons of the NB were selectively destroyed by infuising 2.5 $\mu$g of 192 IgG-saporin immunotoxin into the right lateral ventricle prior to the surgery to implant the chronic stimulating electrode. The toxin, an antibody to the low-affinity NGF receptor linked to a ribosome-inactivating toxin, has been shown to specifically destroy most of the cholinergic neurons of the basal forebrain projecting to the cortex, while sparing the parvalbumin-containing neurons as well as cholinergic neurons that project from the NB to the amygdala [Heckers, S., et al., *J. Neurosci*., 14: 1271 (1994)]. Electrical stimulation of NB and tone presentation was identical for lesioned and non-lesioned animals. The percent of the cortex responding to 19 kHz following pairing in lesioned animals was not significantly different from naive controls (two tailed t-test, n=2).

Even though ACh release is clearly important for NB function, it may be too simplistic to focus exclusively on ACh because only one-third of NB projection neurons are cholinergic [I. Gritti, L. Mainville, M. Mancia, B. E. Jones, *J Comp Neurol*. 383: 163 (1997)]. One-third are GABAergic and the remaining third are uncharacterized. Future work is needed to elucidate the function of concurrent release of these transmitters in cortical plasticity.

Interestingly, the nature of the auditory stimuli paired with NB activation had a profound effect on the selectivity of cortical responses. Sharpness of tuning was quantified as the width of the tuning curve 10 dB above threshold, BW10. When a 250 ms tone was used as the conditioning stimulus, the average BW10 was not significantly different from the average BW10 of control rats (0.93 vs. 1.02 octaves). Conditioning with a temporally modulated stimulus (a train of six short tones of the same frequency) resulted in a mean cortical response that was less selective than controls (1.46 octaves, p<0.0001). Conditioning with two tones engaging different spatial locations on the input array (cochlea) resulted in cortical responses that were more selective than controls (0.70 octaves, p<0.0001). Thus, the paradigm presented herein can result in receptive fields that are narrowed, broadened, or unaltered depending on specific parameters of the acoustic stimulus paired with NB stimulation.

Similar increases and decreases in receptive field sizes have been recorded in the somatosensory and auditory cortices of New World monkeys that have been trained at tactile or auditory discrimination, detection or time-order judgment tasks [Merzenich, M. M. et al., *Cold Spring Harb Symp. Quant. Biol*. 55: 873 (1990)]. A pure tone discrimination task or a task involving a stimulus that moved across several fingers decreased receptive field diameters by approximately 40% [G. H. Recanzone, C. E. Schreiner, M. M. Merzenich, *J. Neurosci*. 13: 87 (1993); W. M. Jenkins, M. M. Merzenich, M. T. Ochs, T. Allard, E. Guic-Robles, *J. Neurophysiol*. 63: 82 (1990)]. In contrast, a task requiring detection of differences in the amplitude modulation rate of tactile stimuli delivered to a constant skin surface increased receptive field diameters by more than 50% [G. H. Recanzonc, M. M. Mcrzenich, W. M. Jenkins, K. A. Grajski, H. R. Dinse, *J. Neurophysiol*. 67: 1031 (1992)].

The mechanisms responsible for remodeling receptive fields in a manner that is appropriate for the particular task an animal practices are not well-defined. One possibility is that top-down instruction from a higher cortical field with explicit knowledge of the goals of the operant task directs cortical plasticity. The fact that our simple paradigm, without any behavioral task, can generate the same receptive field effects induced by extended periods of operant training suggests that the characteristics of the stimuli paired with subcortical neuromodulatory input are sufficient to determine the direction of receptive field alterations. Complex considerations of the network, cellular and molecular mechanisms responsible for the plasticity observed in our studies are outlined, for example, in M. E. Hasselmo, J. M. Bower, *Trends Neurosci*. 16: 218 (1993); M. Sarter, J. P. Bruno. *Brain Res. Rev*. 23: 28 (1997); R. W. Dykes, Can. *J. Physiol, Pharmacol*. 75: 535 (1997).

Adult cortical plasticity appears to be responsible for improvements in a variety of behavioral skills, maintenance of precise sensory representations, in compensation for damage to sensory systems, and functional recovery from central nervous system damage [M. M. Merzenich, G. H. Recanzone, W. M. Jenkins, K. A. Grajski, *Cold Spring Harb. Symp. Quant. Biol*. 55: 873 (1990)]. The results presented herein suggest that activation of the NB is sufficient to guide both large-scale cortical reorganization receptive field reorganization to generate representations that are stable and adapted to an individual's environment by labeling which stimuli are behaviorally important.

EXAMPLE 2

Effect of Experience on the Ability of the Cortex to Respond to Successive Events in Time Neurons in the rat primary auditory cortex (A1) are generally unable to respond to tones presented at more than 12 pulses per second (pps). To test whether the maximum following rate of A1 neurons of adult rats can be modified by experience, trains of brief tones of random carrier frequency but fixed repetition rate were paired with electrical stimulation of the nucleus basalis (NB) 300 to 400 times per day for 20–25 days. This paradigm dramatically altered the temporal response properties of A1 neurons. Pairing NB stimulation with 5 pps stimuli was sufficient to decrease the cortical response to rapidly presented stimuli, while 15 pps pairing significantly increased the maximum cortical following rate. In contrast, when fixed carrier frequency 15 pps trains were paired with NB stimulation, the mean maximum following rate was not significantly increased. These studies demonstrate that NB activation paired with tone trains elicits extensive cortical remodeling of temporal response properties, and that simple differences in spectral and temporal features of the sensory input can drive very different cortical reorganizations.

Most studies of cortical plasticity have documented changes evoked by spatially or spectrally specific stimuli [(Bakin, J. S. & Weinberger, N. M. *Brain Res* 536: 271–286 (1990); Bakin, J. S., South, D. A. & Weinberger, N. M. *Behav Neurosci* 110: 905–913 (1996); Recanzone, G. H., Merzenich, M. M. & Jenkins, W. M. *J Neurophysiol* 67:

1057–1070 (1992); Recanzone, G. H., Merzenich, M. M., Jenkins, W. M., Grajski, K. A. & Dinse, H. R. *J Neurophysiol* 67: 1031–1056 (1992); Recanzone, G. H., Schreiner, C. E. & Merzenich, M. M. *J Neurosci* 13: 87–103 (1993); Weinberger, N. M. *Curr Opin Neurobiol* 3: 570–577 (1993); Xerri, C., Coq, J. O., Merzenich, M. M. & Jenkins, W. M. *J Physiol Paris* 90: 277–287 (1996)]. In a recent experiment of that class, it was demonstrated that the representation of a given tone frequency can be greatly expanded in A1, and that large-scale remodeling of the spectral selectivity of A1 receptive fields (frequency-intensity tuning curves) is achieved by pairing NB activation with tonal stimulation in a non-behaving rat [(Kilgard, M. P. & Merzenich, M. M. *Science* 279: 1714–1718 (1998) (also see studies by Weinberger and colleagues (Bakin, J. S. & Weinberger, N. M. *Proc Natl Acad Sci USA* 93: 11219–11224 (1996); Bjordahl, T. S., Dimyan, M. A. & Weinberger, N. M. *Behav Neurosci* 112: 467–479 (1998)]. NB neurons located in the basal forebrain send cholinergic and GABAergic projections to the entire cortical mantle [Mesulam, M. M., Mufson, E. J., Wainer, B. H. & Levey, A. I. *Neuroscience* 10: 1185–1201 (1983)]. NB stimulation paired with sound stimulation failed to produce significant cortical reorganizations when the acetylcholine-containing cells in the NB were immunolesioned [Kilgard, M. P. & Merzenich, M. M. *Science* 279: 1714–1718 (1998)]. Together, these studies support the long-standing view that the cholinergic projection from the NB is a primary modulatory input source for enabling experience-dependent cortical plasticity.

The data set forth herein are derived from experiments in which NB activation was used to explore the principles governing the plasticity of cortical dynamics as they apply to the representation of the temporal features of rapid, successive stimulus events. One method of describing the capacity of cortical neurons to respond to successive inputs is to derive a "repetition rate transfer function" (RRTF) in which the neural discharge rate is defined as a function of the stimulus repetition rate. Depending upon the type of stimulus modulation used, RRTFs derived for neurons in the primary visual, auditory or somatosensory cortices are low-pass or band-pass in form [De Ribaupierre, F., Goldstein, M. H., Jr. & Yeni-Komshian, G. *Brain Res* 48: 205–225 (1972); Tolhurst, D. J. & Movshon, J. A. *Nature* 257: 674–675 (1975); Movshon, J. A., Thompson, I. D. & Tolhurst, D. J. *J Physiol* (Lond) 283: 101–120 (1978); Schreiner, C. E. & Urbas, J. V. *Hear Res* 32: 49–63 (1988); Schreiner, C. E. & Langer, G. in *Auditory Function* (eds. Edelman, G., Gall, E. & Cowan, M.) 337–362 (John Wiley, New York, 1986); Eggermont, J. J. & Smith, G. M. *J Neurophysiol* 73: 227–245 (1995); Gaese, B. H. & Ostwald, J. *Eur J Neurosci* 7: 438–450 (1995); Hawken, M. J., Shapley, R. M. & Grosof, D. H. *Vis Neurosci* 13: 477–492 (1996)]. In the primary visual and auditory cortical areas, the majority of neurons respond maximally to repeated stimuli when presented at 7–12 pps, responding progressively more poorly at higher repetition rates.

Because the RRTFs of cortical neurons reflect sequences of excitatory and inhibitory cortical circuit events that are set in motion when the cortex is abruptly engaged by a stimulus [De Ribaupierre, F., Goldstein, M. H., Jr. & Yeni-Komshian, G. *Brain Res* 48: 205–225 (1972); Eggermont, J. J. & Smith, G. M. *J Neurophysiol* 73: 227–245 (1995); Gaese, B. H. & Ostwald, J. *Eur J Neurosci* 7: 438–450 (1995); De Ribaupierre, F., Goldstein, M. H. J. & Yeni-Komshian, G. *Brain Res* 48: 185–204. (1972); Kenmochi, M. & Eggermont, J. J. *Neuroreport* 8: 1589–1593 (1997); Chance, F. S., Nelson, S. B. & Abbott, L. F. *J Neurosci* 18: 4785–4799 (1998); Brosch, M. & Schreiner, C. E. *J Neurophysiol* 77: 923–943 (1997); Schreiner, C. E., Mendelson, J., Raggio, M. W., Brosch, M. & Krueger, K. *Acta Otolaryngol Suppl (Stockh)* 532: 54–60 (1997); Cartling, B. *Biol Cybern* 76: 383–395 (1997)], one might predict that this elemental input sampling/recovery property of cortical circuits is immutable. However, a large body of evidence has long argued that temporal response properties of cortical neurons can be substantially altered by experience. For instance, the visual cortex of visually deprived animals responds poorly to stimuli repeated at rates above 5 pps [Beaulieu, C. & Cynader, M. *Brain Res Dev Brain Res* 53: 82–88 (1990); Pizzorusso, T., Fagiolini, M., Porciatti, V. & Maffei, L. *Vision Res* 37: 389–395 (1997)]. Furthermore, the results of several psychophysical studies demonstrating that the ability to discriminate differences in rate, stimulus duration, or interval separating successively presented stimuli can be greatly improved by training are consistent with progressive improvements in cortical processing of temporal information [Woodrow, H. *Psychological Review* 42: 127–152 (1935); Neisser, U. & Hirst, W. *Perception & Psychophysics* 15: 391–398 (1974); Recanzone, G. H., Jenkins, W. M., Hradek, G. T. & Merzenich, M. M. *J Neurophysiol* 67: 1015–1030 (1992); Nagarajan, S. S., Blake, D. T., Wright, B. A., Byl, N. & Merzenich, M. M. *J Neurosci* 18: 1559–1570 (1998); Wright, B. A., Buonomano, D. V., Mahncke, H. W. & Merzenich, M. M. *J Neurosci* 17: 3956–3963 (1997)]. For example, with practice subjects are able to detect brief auditory or visual stimuli that are followed with progressively shorter times by intense masking stimuli, consistent with a several-fold training-induced decrease in cortical integration time [Ahissar, M. & Hochstein, S. *Proc Natl Acad Sci USA* 90: 5718–5722 (1993); Merzenich, M. M. et al. *Science* 271: 77–81 (1996)]. Cortical plasticity studies in monkeys trained to detect changes in amplitude modulation rate recorded sharper and stronger responses to the trained modulation rate [Recanzone, G. H., Merzenich, M. M. & Schreiner, C. E. *J Neurophysiol* 67: 1071–1091 (1992)]. Importantly, this strengthening of cortical responses was strongly correlated with improvement in task performance.

Such changes in temporal properties of cortical responses could result from plasticity of synaptic, intrinsic, or network time constants. For example, plasticity of excitatory synapses on inhibitory neurons [Charpier, S., Behrends, J. C., Triller, A., Faber, D. S. & Korn, H. *Proc Natl Acad Sci USA* 92: 117–120 (1995); Grabauskas, G. & Bradley, R. M. *J Neurophysiol* 79: 595–604 (1998); Hollrigel, G. S., Morris, R. J. & Soltesz, I. *Proc R Soc Lond B Biol Sci* 265: 63–69 (1998)] and of inhibitory synapses themselves [Fischer, T. M., Blazis, D. E., Priver, N. A. & Carew, T. J. *Nature* 389: 860–865 (1997)] may shape the responses of cortical neurons to rapidly successive stimuli in vivo [Buonomano, D. V., Hickmott, P. W. & Merzenich, M. M. *Proc Natl Acad Sci USA* 94: 10403–10408 (1997); Buonomano, D. V. & Merzenich, M. M. *Science* 267: 1028–1030 (1995)]. Additionally, pre-synaptic release probability contributes to the cortical response to successive inputs and is capable of experience-dependent plasticity [Markrarn, H. & Tsodyks, M. *Nature* 382: 807–810 (1996); Tsodyks, M. V. & Markramn, H. [published erratum appears in Proc Natl Acad Sci USA 1997 May 13;94(10):5495]. *Proc Natl Acad Sci USA* 94: 719–723 (1997)]. Together these experiments indicate that the capacity of the cortex to respond to successive events in time is shaped by a succession of excitatory and inhibitory processes, whose dynamics can be modified by experience.

Methods: the following methods were utilized to generate the data presented in Example 2:

Preparation: Platinum bipolar stimulating electrodes were lowered 7 mm below the cortical surface 3.3 mm lateral and 2.3 mm posterior to bregma in ~300 g barbiturate-anesthetized rats of either sex, and cemented into place using sterile techniques approved under UCSF Animal Care Facility protocols. After two weeks of recovery, trains of six 25 msec tones were paired with 200 msec of NB electrical stimulation in a sound-shielded, calibrated test chamber (five days/week). The frequency of the tone was either one of seven frequencies (1.3, 2, 3, 5, 9, 14, or 19 kHz) or was fixed (9 kHz). Tone amplitude was 20–30 dB above the minimum rat hearing threshold [Kelly, J. B. & Masterton, B. *J Comp Physiol Psychol* 91: 930–936 (1977)]. In experiments using multiple carrier frequencies, the frequency of the tones within each train was constant, while the frequencies used from train to train were randomly varied. The tone pips in stimulus trains were presented in a given rat at either 5, 7.5 or 15 pps. Electrical stimulation began with the onset of the fourth tone. The stimulating current level (70–150 $\mu$Amp) was the minimum necessary to desynchronize the EEG during slow wave sleep for 1–2 seconds. Stimulation consisted of 100 pps capacitatively coupled biphasic pulses of 0.1 msec duration. Several microdialysis studies have shown that this stimulation paradigm results in the release of cortical acetylcholine [Jimenez-Capdeville, M. E., Dykes, R. W. & Myasnikov, A. A. *J Comp Neurol* 381: 53–67 (1997); Rasmusson, D. D., Clow, K. & Szerb, J. C. *Brain Res* 594: 150–154 (1992)]. Either cholinergic antagonists or lesions of the cholinergic cells in the NB with 192 immunoglobulin G-saporin are sufficient to block this plasticity generated by NB stimulation [Kilgard, M. P. & Merzenich, M. M. *Science* 279: 1714–1718 (1998); Bakin, J. S. & Weinberger, N. M. *Proc Natl Acad Sci USA* 93: 11219–11224 (1996)]. Tonal and electrical stimuli did not evoke any observable behavioral responses (i.e., did not cause rats to stop grooming, or if sleeping, to awaken).

Electrophysiology: Twenty-four hours after the last pairing, animals were anaesthetized with sodium pentobarbital, the right auditory cortex surgically exposed, and neural responses were recorded with parylene-coated tungsten microelectrodes (FHC #070-02-01, 2 M$\Omega$). Penetration sites were chosen to evenly sample the cortical surface while avoiding blood vessels. To minimize the possibility of experimenter bias or response variability due to variable recording depth, at every penetration site the electrode was lowered to ~550 $\mu$m below the pial surface (layers 4/5), which yielded vigorous driven responses. Frequency/intensity response areas were reconstructed in detail by presenting 45 pure tone frequencies (50 msec duration, 3 msec ramps) at each of 15 sound intensities to the contralateral ear at a rate of 2 stimuli/sec The evoked spikes of a neuron or a small cluster of 2–5 neurons were collected at each site. Primary auditory cortex was defined on the basis of the short latency (8–20 msec) of its evoked neuronal spike responses and its continuous tonotopy (BF increases from posterior to anterior). Responsive sites that exhibited clearly discontinuous best frequencies and (a) either long latency responses, (b) high thresholds, or that (c) had very broad tuning were considered to be non-A1 sample sites, and were not included in these sample data.

To determine the RRTF for each site, six tones (25 msec with 5 msec ramps, 70 dB SPL) were presented 12 times at each of 16 repetition rates. To minimize adaptation effects, repetition rates were randomly interleaved and two seconds of silence separated each train. The two-second interval between trains allowed the response strength to 0.5 pps trains to be approximated. The frequencies of tones in the trains for defining the RRTF in the mapping study were the frequency of the seven used in pairing that was closest to the best frequency for neurons sampled at each site. To reduce the variability resulting from different numbers of neurons included in different "multi-unit" responses recorded in this study, response amplitude was normalized using the number of spikes evoked at each site to a tone in isolation. The normalized RRTF was defined as the average number of spikes evoked for each of the last five tones in the train divided by the number of spikes evoked by the first tone in the train. Thus, a normalized spike rate of one indicates that at the given repetition rate each of the tones in the train, on average, evoked the same number of spikes as the first tone. Values greater than one indicate facilitation; values less than one indicate response adaptation. Only spikes occurring from 5–40 msec after each tone onset were used to calculate the RRTF. RRTF data could not be viewed on-line and were analyzed only after each experiment was completed. All analyses was automatized, and were therefore not subject to experimenter bias or error. The effect of NB pairing on mean RRTF across all conditions was determined with analysis of variance; pairwise comparisons were analyzed by Fisher's PLSD.

As a result of barbiturate anesthesia the modulation of responses recorded in this study may not be identical to the responses of awake animals.

Data:

In this study, NB activation was paired with temporally modulated acoustic stimuli to investigate plasticity of the cortical representation of time-varying information. Stimulating electrodes were chronically implanted in the right NB of 15 adult rats. After recovery, animals were placed in a sound attenuation chamber and a train of six tone bursts paired with NB stimulation during daily sessions. Tone trains and NB stimulation occurred randomly every 8–40 seconds and was repeated three to four hundred times per day for 20–25 days. Rats were unanesthetized and unrestrained throughout this procedure. The train repetition rate for each rat was presented at a fixed rate of 5, 7.5 or 15 pps. The tonal (carrier) frequency was varied randomly trial by trial. The seven carrier frequencies that were applied extended across most of the frequency range represented in the primary auditory cortex (A1) of the rat. Twenty-four hours after the last pairing session, each animal was anesthetized, and the responses of A1 neurons were recorded from 30–60 microelectrode penetrations distributed evenly across A1. Frequency-intensity tuning curves and RRTFs were derived to characterize the spectral and temporal response properties of neurons in every penetration.

In naïve animals, at repetition rates up to about 9 pps, each brief tone generally evoked the same number of spikes from A1 neurons as did the first tone in the train. At repetition rates from 9 to 14 pps, the number of spikes per tone fell off rapidly and only neurons at rare sites responded at all to rates above 15 pps.

In experimental rats in which 15 pps stimuli of variable carrier frequencies were paired with NB stimulation, there was a dramatic alteration of the temporal responses of cortical neurons recorded all across A1. Although no specific response peak emerged at 15 pps, the cut-off rate of low-pass RRTFs in A1 rose significantly in the majority of sampled neurons. In striking contrast to control rats, the average neuron in these samples exhibited strong responses to repetition rates between 10 and 20 pps. The increase in the neural response to 15 pps trains after pairing was highly significant (p<0.0001). The high-rate slope of the average RRTF shifted higher, reflecting a strong response improvement across a broad range of higher modulation frequencies.

To determine whether or not NB-induced temporal plasticity is specific to the repetition rate of the paired acoustic stimulus, 5 pps trains were paired with NB activation. The normalized evoked response to stimuli repeated at 5 pps was significantly increased (p<0.01), resulting in RRTF's with bandpass characteristics (maxima approximately corresponding to the 5 pps modulation rate applied during sound stimulus/NB pairing). Interestingly, 5 pps pairing resulted in two distinct classes of cortical responsiveness to faster rates. In three of four animals, the entire RRTF was shifted leftward causing significantly decreased maximum following rates. In the remaining animal, 75% of sites exhibited strong facilitation to both 5 and 10 pps stimuli, but poor responses to stimuli repeated at 7.5 pps (data not shown). Thus NB-induced plasticity reliably increased the strength of the cortical response to stimuli presented at the paired rate, even though RRTF plasticity can take on at least two forms.

Pairing 7.5 pps stimuli of randomly-varied carrier frequency with NB stimulation resulted in a selective strengthening of the cortical response to stimuli repeated at rates near 7.5 pps. The mean RRTF again took on a bandpass form, with a substantially stronger-than-normal response to modulated stimuli emerging at the paired stimulus rate. The normalized response of 1.2 indicates that 20% more spikes were evoked on average by each tone in the context of a 7 pps train compared to the same tone in isolation.

As reported previously, pairing tones presented at 15 pps with a constant carrier frequency of 9 kHz resulted in a dramatic enlargement of the region of A1 representing 9 kHz in every animal [Kilgard, M. P., and M. M. Merzenich. *Science* 279: 1714–8, (1998)]. Surprisingly, pairing trains of 9 kHz tones repeated at 15 pps did not result in the rightward shift in the mean RRTF that resulted from pairing NB stimulation with multiple frequency trains repeated at 15 pps. No significant alteration in the mean response to the paired repetition rate (15 pps) was detected in the population RRTF analysis (0.27 vs. 0.28, p>0.5; one-way ANOVA). Although it is unclear how topographic map reorganization and temporal plasticity are related, it is interesting to note that pairing random-frequency 15 pps trains with NB stimulation resulted in a significant increase in the maximum stimulus following rate of cortical neurons, but generated no systematic alterations of the A1 map of frequency.

Discussion:

Paired NB and sensory stimulation provides a simple model with which to study the rules that operate in the cortex to transform sensory input structure and schedules into distributed cortical response patterns. Previous studies have focused on the plasticity of the cortical representation of spectral information, and have demonstrated that cholinergic modulation is sufficient to shift A1 tuning curves toward the frequency paired with NB stimulation [Kilgard, M. P. & Merzenich, M. M. *Science* 279: 1714–1718 (1998); Bakin, J. S. & Weinberger, N. M. *Proc Natl Acad Sci USA* 93: 11219–11224 (1996); Bjordahl, T. S., Dimyan, M. A. & Weinberger, N. M. *Behav Neurosci* 112: 467–479 (1998); Metherate, R. & Weinberger, N. M. *Brain Res* 480: 372–377 (1989); McKenna, T. M., Ashe, J. H. & Weinberger, N. M. *Synapse* 4: 30–43 (1989)]. As shown herein, the temporal response properties of A1 neurons can be dramatically altered to broadly refine or to degrade the capacity of the cortex to respond to rapidly successive input events. It has also been shown that this plasticity manifests a large capacity to exaggerate the representation of specific, heavily presented sensory input rates. Finally, it has been demonstrated that A1 neuronal networks (a) can generate spectrally and temporally selective responses; (b) can reorganize topographically organized representations of tone frequency while generating no evident change in the representation temporal information; (c) or vice versa—all as an apparent function of the spectrotemporal structures and schedules of sensory inputs.

This striking capacity for learning-based revision of the basic integration/segmentation times of the cortical processing machinery could result from plasticity of synaptic time constants, of intrinsic temporal characteristics, and/or network dynamics [De Ribaupierre, F., Goldstein, M. H., Jr. & Yeni-Komshian, G. *Brain Res* 48: 205–225 (1972); Eggermont, J. J. & Smith, G. M. *J Neurophysiol* 73: 227–245 (1995); Kemnochi, M. & Eggermont, J. J. *Neuroreport* 8: 1589–1593 (1997); Markram, H. & Tsodyks, M. *Nature* 382: 807–810 (1996); Dinse, H. R., et al. *Int J Psychophysiol* 26: 205–227 (1997)]. Paired-pulse facilitation and slow inhibitory potentials, for example, almost certainly play an important role in the cortical recovery of responsivity following any brief stimulation [De Ribaupierre, F., Goldstein, M. H., Jr. & Yeni-Komshian, G. *Brain Res* 48: 205–225 (1972); Brosch, M. & Schreiner, C. E. *J Neurophysiol* 77: 923–943 (1997); Schreiner, C. E., Mendelson, J., Raggio, M. W., Brosch, M. & Krueger, K. *Acta Otolaryngol Suppl* (*Stockh*) 532: 54–60 (1997); Buonomano, D. V., Hickrnott, P. W. & Merzenich, M. M. *Proc Natl Acad Sci USA* 94: 10403–10408 (1997); Buonomano, D. V. & Merzenich, M. M. *Science* 267: 1028–1030 (1995); Markram, H. & Tsodyks, M. *Nature* 382: 807–810 (1996); Abbott, L. F., Varela, J. A., Sen, K. & Nelson, S. B. *Science* 275: 220–224 (1997)]. NB-induced plasticity stimulation will provide a powerful experimental approach for relating the cortical representation of temporal information to changes in basic cortical dynamics that shape the cortical responses to time-varying stimuli.

EXAMPLE 3

Effect on Cortical Plasticity of Variations in Frequency and Delivery Rate of Auditory Stimulus Paired with Electrical Stimulation of the Nucleus Basalis Repeated electrical stimulation of the nucleus basalis (NB) paired with tonal stimuli for several hours each day for four weeks generated large-scale changes in the representations of the paired acoustic stimuli in the primary auditory cortex (A1) of adult rats. By systematically varying several features of the auditory stimulus, we explored how the sensory input influences cortical plasticity. The region of the cortical representation that expanded was specific to the frequency of the paired tone. The introduction of a delay between NB stimulation and the paired auditory stimulus decreased the specificity of the reorganization. The receptive field size (frequency bandwidth) of A1 neurons varied systematically as a function of both the temporal modulation rate and carrier-frequency variability of the paired auditory stimulus. Frequency selectivity was decreased after pairing NB stimulation with a rapid train of short 9 kHz tones, and increased after pairing unmodulated tones of different frequencies. Observed expansions of the functionally-defined borders of A1 and increased cortical excitability were also sensitive to particular features of the auditory stimulus that was paired with NB activation.

These results suggest that cortical plasticity can be shaped by the structure and schedule of inputs that co-occur with nucleus basalis activity.

The major source of cholinergic input to the neocortical mantle arises from neurons located in the basal forebrain, including the ventromedial aspect of the globus pallidus and the dorsal aspect of the substantia innominata. This region is called the Ch4 sector of the rodent central cholinergic system and includes the nucleus basalis (NB) [Mesulam, M. M. et al.(Ch1–Ch6) *Neuroscience* 10: 1185–201, (1983)]. Only one third of NB projection neurons are cholinergic [Gritti, I., L. et al. *J Comp Neurol* 383: 163–77 (1997)]. One third are GABAergic, and the remaining third are uncharacterized. NB neurons project ipsilaterally to all of the neocortex, as well as to the amygdala and the reticular nucleus of the thalamus [Levey, A. I. et al. *Neurosci Lett* 74: 7–13 (1987); Mesulam, M. M. et al. (Ch1–Ch6) *Neuroscience* 10: 1185–201 (1983)]. NB receives inputs from the amygdala, ventral tegmentum, frontal cortex, hypothalamus, and from a number of brainstem nuclei [Haring, J. H., and R. Y. Wang. *Brain Res* 366: 152–8 (1986)].

Several lines of evidence suggest that cholinergic projections from NB to the cerebral cortex play an important role in gating cortical plasticity. Lesions of the NB or the application of cholinergic antagonists are both sufficient to disrupt map plasticity in visual and somatosensory cortex. Bear and Singer blocked the ocular dominance (OD) shift that normally follows temporary eyelid suture by depleting cortical acetylcholine and norepinephrine with 6-hydroxydopamine (6-OHDA) [Bear, M. F., and W. Singer. *Nature* 320: 172–6 (1986)]. Continual application of muscarinic antagonists also blocks OD plasticity [Gu, Q., and W. Singer. *Eur J Neurosci* 5: 475–85 (1993)]. Cholinergic modulation is also required for map plasticity in adult animals. Excitotoxic lesions of NB are sufficient to inhibit cortical reorganization following digit amputation or nerve section [Juliano, S. L., W. Ma, and D. Eslin. *Proc Natl Acad Sci USA* 88: 780–4 (1991);]. Webster, H. H. et al. *Somatosens Mot Res* 8: 327–46 (1991a)]. Lesion precision has been substantially improved with the development of the cholinergic immunotoxin IgG 192-saporin (a monoclonal antibody to the low-affinity NGF receptor linked to the ribosomal toxin saporin). These highly selective lesions of cholinergic neurons in the NB prevent the plasticity that results from trimming all but two whiskers in adult rats [Baskerville, K. A. et al. *Neuroscience* 80: 1159–69 (1997); Sachdev, R. N. et al. *J Neurophysiol* 79: 3216–28 (1998)] or from follicle removal in newborn rats [Zhu, X. O., and P. M. Waite. *Cereb Cortex* 8: 63–72 (1998)]. Such experiments provide strong evidence that NB is necessary for cortical map reorganizations in both young and adult animals.

Cholinergic lesions or cholinergic receptor antagonists disrupt learning and memory in both animals and humans (see [Hasselmo, M. E. *Behav Brain Res* 67: 1–27 (1995)] for review). Cholinergic lesions in rats cause performance decrements in tasks involving short-term memory, spatial navigation, and passive avoidance [Riekkinen, P., Jr. et al. *Neuroscience* 47: 823–31 (1992); Steckler, T. et al. *Neuroscience* 66: 101–14 (1995); Winkler, J. et al. *Nature* 375: 484–7 (1995)]. Butt and Hodge showed that NB lesions have significant effects on the acquisition phase of a visual discrimination task, but only a modest effect on the performance of pre-trained rats [Butt, A. E., and G. K. Hodge. *Behav Neurosci* 109: 699–713 (1995)]. Consistent with an important role of cholinergic modulation in learning, microdialysis studies have shown that acetylcholine release is enhanced during acquisition of an operant behavior, but not during performance in pretrained animals [Orsetti, M., F. Casamenti, and G. Pepeu. *Brain Res* 724: 89–96 (1996)]. Acquas and colleagues demonstrated that extracellular acetylcholine levels are increased by novel stimuli and by stimuli associated with footshock, but are not increased by the same stimuli in habituated animals [Acquas, E., C. Wilson, and H. C. Fibiger. *J Neurosci* 16: 3089–96 (1996)].

Single unit recordings in rats, rabbits, and monkeys have shown that NB neurons respond to behaviorally arousing stimuli [Pirch, J. H. *Brain Res Bull* 31: 73–83 (1993); Richardson, R. T., and M. R. DeLong. *Adv Exp Med Biol* 295: 233–52 (1991); Whalen, P. J., B. S. Kapp, and J. P. Pascoe. *J Neurosci* 14: 1623–33 (1994)]. The minimum latency for NB activation is approximately 50 msec. Richardson and DeLong demonstrated that an individual NB neuron can respond to both aversive and rewarding stimuli of different modalities. The response of these neurons is often graded by the size of the reward. NB neurons can be conditioned to respond to innocuous stimuli that become associated with reward. It has been proposed that acetylcholine serves as a reinforcement signal to guide cortical plasticity [Hasselmo, M. E. *Behav Brain Res* 67: 1–27 (1995); Singer, W. *Eur Arch Psychiatry Neurol Sci* 236: 4–9 (1986); Weinberger, N. M. *Curr Opin Neurobiol* 3: 570–7 (1993); Woody, C. D. *Fed Proc* 41: 2160–8 (1982)].

This hypothesis has been supported by a series of experiments demonstrating that pairing of electrical stimulation of NB or iontophoresis of acetylcholine with sensory stimuli is sufficient to generate cortical plasticity. Hennevin and colleagues recorded the responses of auditory cortex neurons before and after NB stimulation paired with a pure tone chosen to evoke a consistent cortical response [Edeline, J. M., B. Hars, C. Maho, and E. Hennevin. *Exp Brain Res* 97: 373–86 (1994a); Edeline, J. M., C. Maho, B. Hars, and E. Hennevin. *Brain Res* 636: 333–7 (1994b); Hars, B., C. Maho, J. M. Edeline, and E. Hennevin. *Neuroscience* 56: 61–74 (1993)]. Pairing increased cortical responses by up to 100% in the hemisphere ipsilateral to the stimulation site, without inducing any significant change in the contralateral hemisphere. In these experiments, NB-induced plasticity could be generated in awake, anesthetized or sleeping rats. Bakin and Weinberger showed that a similar stimulation paradigm resulted in systematic shifts of frequency receptive fields, that can last up to 30 minutes [Bakin, J. S., and N. M. Weinberger. *Proc Natl Acad Sci USA* 93: 11219–24 (1996). Metherate and Ashe showed that the plasticity was much decreased when cortical input and NB stimulation were separated by more than a second [Metherate, R., and J. H. Ashe. *Brain Res* 559: 163–7 (1991); Metherate, R., and J. H. Ashe. *Synapse* 14: 132–43 (1993)]. NB stimulation has also been used to generate plasticity in the somatosensory cortex of rats, cats and raccoons [Howard, M. A., 3rd, and D. J. Simons. *Exp Brain Res* 102: 21–33 (1994); Tremblay, N., R. A. Warren, and R. W. Dykes. *J Neurophysiol* 64: 1212–22 (1990); Webster, H. H., D. D. Rasmusson, R. W. Dykes, R. Schliebs, W. Schober, G. Bruckner, and D. Biesold. *Brain Res* 545: 292–6 (1991b)].

Atropine, a cholinergic antagonist, can block the plasticity generated by NB stimulation. Direct iontophoresis of acetylcholine or cholinergic agonists can also generate plasticity that is specific to the frequency of the paired auditory stimulus [McKenna, T. M., J. H. Ashe, and N. M. Weinberger. *Synapse* 4: 30–43 (1989); Metherate, R., and N. M. Weinberger. *Brain Res* 480: 372–7 (1989); Metherate, R., and N. M. Weinberger. *Synapse* 6: 133–45 (1990)]. Collectively, these results clearly demonstrate that cholinergic modulation can profoundly affect short term-plasticity.

Recent experiments have expanded these findings to explore the long-term effects of repeated daily pairing of NB stimulation with tonal stimuli [Kilgard, M. P., and M. M.

Merzenich. *Science* 279: 1714–8 (1998a); Kilgard, M. P., and M. M. Merzenich. *Nat Neurosci* 1: 727–731 (1998b)]. Electrical stimulation of NB paired with tonal stimuli each day for a month generated long-term (>24 hours) reorganization of the cortical map of sound frequency. Additionally, the maximum following rate of cortical neurons were increased or decreased depending on the repetition rate paired with NB stimulation (5 vs. 15 pulses/second). Interestingly, variability of the carrier frequency (randomized vs. fixed) had a significant effect on the type of temporal plasticity generated by NB stimulation. This result suggests that representational plasticity of one stimulus dimension can be affected by other stimulus dimensions or schedules.

In this current study, several features of the auditory stimuli were systematically varied to further explore how the structures and schedules of delivery of auditory inputs paired with cholinergic modulation are expressed in the reorganization of A1 tuning curves and best frequency maps.

Methods:

NB stimulating electrodes were implanted in thirty-seven pentobarbital anesthetized (50 mg/kg) rats (~300 g). Rats received prophylactic treatment with ceftizox antibiotic (20 mg/kg), dexamethazone (4 mg/kg) and atropine (1 mg/kg). Platinum bipolar stimulating electrodes (SNE-200, Rhodes Medical Instruments, Inc., Woodland Hills, Calif.) were lowered 7.0 mm below the cortical surface 3.3 mm lateral and 2.3 mm posterior to bregma, and cemented into place using sterile techniques approved under UCSF animal care protocols. Three bone screws were used to anchor the electrode assembly. Leads were attached to screws over the cerebellum and cortex so that the global EEG could be monitored.

After two weeks of recovery, tonal stimuli were paired with NB electrical stimulation in a sound-shielded, calibrated test chamber (five days/week) for one month. Animals were placed in a 25 by 25 cm wire cage in the middle of 60 by 70 cm box lined with 3 inch acoustic foam. The cage was positioned 20 cm below the audio speaker. A small 4-pin connector attached to a swivel was used to record the EEG and to deliver short current pulses. Each animal received three to five hundred pairings of tones and NB stimulation per day. Interstimulus intervals varied randomly from 10 to 30 seconds. Ten rats received NB stimulation paired with a 70 dB SPL tone with a fixed frequency (4, 9, 19 kHz). In five rats, two different randomly interleaved tone frequencies were paired with NB stimulation (4 & 14 or 9 & 19 kHz). In four rats, a train of six short 9 kHz tones presented at 15 pulses per second (pps) were paired with NB stimulation. In ten rats, trains of short tones applied at a constant tone frequency which varied randomly from trial to trial (1.3, 2, 3, 5, 9, 14, or 19 kHz). The repetition rate of the tones was fixed for each animal (5, 7.5, and 15 pps, n=4, 2, and 4 rats, respectively). All tones had 3 msec onset and offset ramps.

To establish the specificity of NB pairing, many animals were also stimulated with other tones that were not paired with NB stimulation. Half of the animals in the single-frequency group were also presented, on the same schedule, with two other tone frequencies (see Table 1). There were no unpaired stimuli delivered to the 9 kHz/15 pps rats. The multiple frequency train groups heard one of each of the multiple frequencies tone pips presented in isolation without NB stimulation as often as they heard each train that was paired with NB stimulation.

TABLE 1

Experimental Manipulations

| Experiment Group | Auditory stimuli Paired with NB Stimulation | Unpaired Stimuli | Number of Rats | Number of A1 Sites |
| --- | --- | --- | --- | --- |
| Naive | ∅ | ∅ | 9 | 440 |
| One Freq | 4 kHz - 200 msec 70 dB | [2 & 9 kHz] | 4 | 242 |
| One Freq | 9 kHz - 200 msec 70 dB | [4 & 19 kHz] | 4 | 233 |
| One Freq | 19 kHz - 200 msec 70 dB | [4 & 9 kHz] | 2 | 112 |
| Out of phase | ∅ | 19 kKz - 200 msec 70 dB 10 sec before NB stimulation | 4 | 206 |
| Two Freq | 4 & 14 kHz - 200 msec 70 dB | 9 & 19 kHz | 2 | 90 |
| Two Freq | 9 & 19 kHz - 200 msec 70 dB | 4 & 14 kHz | 3 | 119 |
| Lesion | 19 kHz - 200 msec 70 dB - NB immuno-lesion | ∅ | 2 | 95 |
| 15 pps 9 kHz | 15 pps train of six tones, 9 kHz - 25 msec | ∅ | 4 (6) | 224 (332) |
| 15 pps multi | 15 pps train of six tones, multiple frequency - 25 msec | single tones of multiple frequency | 4 | 223 |
| 7.5 pps multi | 7.5 pps train of six tones, multiple frequency - 25 msec | single tones of multiple frequency | 2 | 92 |
| 5 pps multi | 50 pps train of six tones, multiple frequency - 25 msec | single tones of multiple frequency | 4 | 175 |

When simple unmodulated tones were used as the auditory stimulus, electrical stimulation began 50 msec after tone onset in half the experiments and 200 msec before tone onset in the other half. When tone trains were used, stimulation occurred simultaneously with the onset of the fourth tone in trains. In four animals, 19 kHz tones were presented ten seconds after each NB stimulation.

The current level (70–150 $\mu$Amp) for NB stimulation was chosen for each animal to be the minimum necessary to desynchronize the EEG during slow wave sleep for 1–2 seconds. Stimulation consisted of 20 capacitatively coupled biphasic pulses (0.1 msec pulse width, 100 pulses per second). Several microdialysis studies have shown that this stimulation paradigm results in release of cortical acetylcholine [Jimenez-Capdeville, M. E., R. W. Dykes, and A. A. Myasnikov. *J Comp Neurol* 381: 53–67 (1997); Rasmusson, D. D., K. Clow, and J. C. Szerb. *Brain Res* 594: 150–4 (1992)]. Either cholinergic antagonists or lesions of the cholinergic cells in the NB with IgG 192-saporin are sufficient to block the plasticity generated by NB stimulation

[Bakin, J. S., and N. M. Weinberger. *Proc Natl Acad Sci USA* 93: 11219–24 (1996); Kilgard, M. P., and M. M. Merzenich. *Science* 279: 1714–8 (1998a)]. Tonal and electrical stimuli did not evoke any observable behavioral responses, i.e., did not cause rats to stop grooming, or awaken, if sleeping.

Cholinergic neurons of the NB were selectively destroyed in two animals by infusion of 2.5 μg of 192 IgG -saporin (Chemical International, Inc.; Temecula, Calif.) into the right lateral ventricle during the surgery to implant the NB stimulating electrode. Injections were made with a 10 μL hamilton syringe guided by stereotaxic coordinates (AP −1.0, ML +4.5, DV −4.5 mm relative to bregma). The 5 μL volume was delivered over 5 minutes and the syringe was kept in place for an additional five minutes. The 192 IgG monoclonal antibody binds to the low-affinity nerve growth factor receptor on the surface of cholinergic NB neurons and is internalized. The toxin conjugated to the antibody causes cell death. Lesioned animals were given 5–10 mL of saline i.p. daily during the recovery period. Standard ACHE staining techniques were used to confirm cortical depletion.

This study is based on neuronal spike data collected from 2,359 microelectrode penetrations into the right primary auditory cortex in 46 adult female Sprague-Dawley rats. Surgical anesthesia was induced with sodium pentobarbital (50 mg/kg). Throughout the surgical procedures and during the recording session, a state of areflexia was maintained with supplemental doses of dilute pentobarbital (8 mg/ml; i.p.). The trachea was cannulated to ensure adequate ventilation and to minimize breathing-related noises. The skull was supported in a head holder that left the ears unobstructed. The cisternae magnum was drained of CSF to minimize cerebral edema. After reflecting the temporalis muscle, auditory cortex was exposed via a wide craniotomy and the dura mater was resected. The cortex was maintained under a thin layer of viscous silicon oil to prevent desiccation. The location of each penetration was reproduced on a 40× digitized image of the cortical surface microvasculature.

The primary auditory cortex was defined on the basis of its short latency (8–20 msec) responses and its continuous tonotopy (preferred tone frequency increased from posterior to anterior). Responsive sites that exhibited clearly discontinuous best frequencies and either long latency responses, unusually high thresholds, or very broad tuning were considered to be non-A1 sites. Penetration sites were chosen to avoid damaging blood vessels while generating a detailed and evenly spaced map. The boundaries of the map were functionally determined using non-responsive and non-A1 sites.

Recordings were made in a shielded, double-walled sound chamber (IAC). Action potentials were recorded simultaneously from two Parylene-coated tungsten microelectrodes (FHC, Inc., 250 μm separation, 2 MΩ at 1 kHz) that were lowered orthogonally into the cortex to a depth of ~550 μm (layers IV/V). The neural signal was filtered (0.3 to 8 kHz) and amplified (1000×). Action potential waveforms were recorded whenever a set threshold was exceeded, allowing off-line spike sorting using Autocut software (Datawave). Although most responses in this study represented the spike activity of several neurons, single units were separated when possible, confirming that single units exhibited tuning that was qualitatively similar to multi-unit response samples. To minimize experimenter-induced sampling bias the experimenter was blind to the frequency(ies) paired with NB stimulation.

Monaural stimuli were delivered to the left ear via a calibrated ear phone (STAX 54) positioned just inside the pinnae. Frequencies and intensities were calibrated using a B&K sound level meter and a Ubiquitous spectrum analyzer. Auditory frequency response tuning curves were determined by presenting 45 frequencies spanning 3–4.5 octaves centered on the approximate best frequency of the site. Each frequency was presented at 15 intensities ranging between 0 and 75 dB (675 total stimuli). Tuning curve tones were randomly interleaved and separated by 500 msec. All tonal stimuli used during the acute phase of this study were 25 msec long, including 3 msec rise and fall times.

Tuning curve parameters were defined by an experienced blind observer using custom software that displayed raw spike data without reference to the frequencies and intensities that generated the responses. For each tuning curve, best frequency, threshold, bandwidth (10, 20, 30 and 40 dB above threshold), and latency data were recorded. Best frequency (BF) is the frequency that evokes a consistent neural response at the lowest stimulus intensity. The minimum latency was defined as the time from stimulus onset to the earliest consistent response for any of 15 intensities of the three frequencies that were nearest the BF (45 stimuli).

Voronoi tessellation was used to generate polygons from a set of non-uniformly spaced points such that every point in the polygon was nearer to the sampled point than to any other. Tessellation allowed area estimation from discretely sampled penetrations by assuming that each location on the cortical surface had the response characteristics of the closest sampled point [Kilgard, M. P., and M. M. Merzenich. *Science* 279: 1714–8 (1998a)]. The percent of the cortical surface responding to a given stimulus was estimated by adding all of the areas of the penetrations that included the stimulus within their receptive field, divided by the total responsive (A1) area. This measure is fairly insensitive to non-homogenous sampling densities because each penetration in a more densely sampled area has a proportionally smaller contribution, and vice versa.

Results:

Stimulation of NB paired with tonal stimuli has been demonstrated to be sufficient to significantly enhance cortical responses. These enhanced responses have been described in two ways: as an increase in the strength of the evoked response to the paired stimulus, and as an increase in the number of cortical neurons engaged by the paired stimulus [Bakin, J. S., and N. M. Weinberger. *Proc Natl Acad Sci USA* 93: 11219–24 (1996); Edeline, J. M., B. Hars, C. Maho, and E. Hennevin. *Exp Brain Res* 97: 373–86 (1994a); Edeline, J. M., C. Maho, B. Hars, and E. Hennevin. *Brain Res* 636: 333–7 (1994b); Hars, B., C. Maho, J. M. Edeline, and E. Hennevin. *Neuroscience* 56: 61–74 (1993); Kilgard, M. P., and M. M. Merzenich. *Science* 279: 1714–8 (1998a)]. The number of neurons participating in the cortical representation of a conditioned tone can be increased by 1) receptive field plasticity that shifts the best frequency (BF) of primary auditory cortex (A1) neurons towards the paired frequency; 2) decreased selectivity of frequency tuning, and/or 3) expansion of primary auditory cortex boundaries. In this study, we examined the cortical plasticity generated by NB stimulation paired with nine different stimulus sets, and observed that cortical representations were enhanced by different combinations of all three of these effects, depending on the nature of the NB-paired auditory stimuli.

Detailed maps of A1 were reconstructed for 9 naïve rats and 37 NB-stimulated rats. A1 was distinguished from surrounding auditory fields by its tonotopy and characteristic short-latency responses. Continuous topography and an even distribution of preferred frequencies was observed in every control animal. Rat A1 tuning curves were V-shaped and had monotonic intensity response functions [Sally, S. L., and J.

B. Kelly. *J Neurophysiol* 59: 1627–38 (1988)]. The average bandwidths for A1 responses in naive animals were 0.97±0.4 and 1.42±1.0 octaves (mean±SD) at 10 and 30 dB above threshold, respectively.

NB Stimulation Paired with Sinole Tone Frequency

Repeated electrical activation of NB paired with an unmodulated pure tone (4, 9, or 19 kHz) five days per week for one month was sufficient to generate substantial reorganization of the A1 frequency map. The cortical response to the paired frequency was enhanced in all ten animals. After pairing, an increased number of penetrations had BF's near the paired frequency, compared to naive controls. Clustering of BF's indicates that the frequency tuning of cortical neurons were reorganized, such that BF's shifted toward the paired frequency. The pattern of BF shifts varied substantially from animal to animal. In two of the four 9 kHz paired animals, for example, neurons predominately representing higher frequencies appeared to shift their tuning curves lower, while the opposite appears to have occurred in two other rats. Thus, the cortical representation of the paired frequency was increased as a result of BF shifts toward the conditioned frequency, while there was significant variability in the specific map changes that led to the distortions.

The number of cortical neurons activated by the paired stimulus was also increased by decreasing the selectivity of frequency tuning. Pairing NB stimulation with a fixed tone frequency increased receptive field bandwidth by up to 20%. Plasticity of best frequency and bandwidth combined to increase the percent of A1 that responded to the paired tone frequency (Table 2). The percent of cortex responding to the paired frequency was increased by up to two-fold, compared to naïve controls. The BF shifts that resulted in increases in the percent of cortex responding were greatest for frequencies near the paired frequency. Interestingly, increased bandwidth changes in A1 were not frequency-specific.

paired frequency, but were not paired with NB stimulation. These additional frequencies did not appear to affect the tuning curves shifts toward the paired frequency or the expansion of the borders of A1, but interestingly, prevented the 20% decrease in frequency selectivity that followed single-tone pairing without unpaired frequency stimulation in A1 in all recorded rats.

Nucleus Basalis Lesions

Specific immunolesions of neurons within NB were used to demonstrate that the plasticity evoked by NB stimulation was specific to the cholinergic system. The toxin, 192 immunoglobulin G-saporin, destroys the cholinergic NB neurons that project to the cortex. The lesion does not destroy the GABAergic or other neurons that make up two-thirds of the projection from NB to the cortex in the intact animal, and also spares the cholinergic neurons that project to the amygdala [Heckers, S., T. Ohtake, R. G. Wiley, D. A. Lappi, C. Geula, and M. M. Mesulam. *J Neurosci* 14: 1271–89 (1994)]. Electrical stimulation of the immunolesioned NB paired with 19 kHz did not result in a significant increase in the number of neurons responding to 19 kHz (32±0.3% versus 28±4%, p>0.5) and did not significantly increase the functionally defined area of A1 (2.4±0.1 mm$^2$). However, frequency bandwidths were somewhat increased following NB immunolesioning and basal forebrain stimulation.

Relative Timing of Electrical and Auditory Stimulation

To investigate the importance of the relative timing between NB activation and tone onset, two different timings were used (stimulation onset 50 msec after or 200 msec before tone onset). These two timings resulted in indistinguishable plasticity effects, and the two timings were grouped in all further analyses. Four animals received NB stimulation that was separated from the auditory stimulus by ten seconds. In these animals, the area of A1 was not significantly different from controls and tuning curves

TABLE 2

A1 Frequency Map Reorganizations

| Group | Percent of A1 Responding | | | | A1 Area Responding-mm$^2$ | | | |
|---|---|---|---|---|---|---|---|---|
| | 2 kHz | 4 kHz | 9 kHz | 19 kHz | 2 kHz | 4 kHz | 9 kHz | 19 kHz |
| Control | 18 ± 4.1 | 17.6 ± 3.4 | 18.9 ± 1.8 | 27.8 ± 3.7 | .35 ± .09 | .34 ± .08 | .36 ± .06 | .52 ± .10 |
| 4 kHz | 23.4 ± 9.1 (1.3) | 35.4 ± 4.0* (2.0) | 28.7 ± 5.2 (1.5) | 37.9 ± 3.2 (1.4) | .62 ± .14 (1.8) | 1.15 ± .37* (3.4) | .98 ± .35* (2.7) | 1.19 ± .28* (2.2) |
| 9 kHz | 16.2 ± 7.0 (0.9) | 26.4 ± 10.4 (1.5) | 32.7 ± 5.5* (1.7) | 30.1 ± 10.5 (1.1) | .45 ± .16 (1.3) | .75 ± .24 (2.2) | 1.07 ± .27* (3.0) | 1.12 ± .47 (2.1) |
| 19 kHz | 9.5 ± 47 (0.5) | 8.6 ± 4.9 (0.5) | 15.1 ± 8.4 (0.8) | 47.0 ± 4.7* (1.7) | .20 ± .07 (0.5) | .17 ± .08 (0.5) | .31 ± .13 (0.9) | 1.07 ± .29* (2.0) |
| 19 kHz Out | 25.9 ± 3.4 (1.4) | 28.6 ± 5.6 (1.6) | 32.9 ± 6.9* (1.7) | 44.5 ± 4.2* (1.6) | .6 ± .13 (1.7) | .71 ± .25 (2.1) | .82 ± .30 (2.3) | 1.05 ± .19* (2.0) |

The data in Table 2 shows the size of cortical sector engaged, expressed as percent of A1 surface responding and as area in mm$^2$ in NB stimulated animals and naïve controls. Mean ± standard error.
* means p < 0.05. The numbers in parenthesis is the ratio of paired to control.

In addition to increases in the relative proportion of A1 that responded to a specific tonal stimulus paired with NB activation, the absolute area of A1 was also significantly increased by pairing NB activation with tonal stimuli. This increase in A1 area was based on the well-established functional definition that the primary auditory field has phasic, short-latency responses to tones and a continuous tonotopy. The three observed classes of cortical reorganization combined to result in an up to three-fold increase in the cortical area activated by the paired stimulus compared to controls (Table 2).

As a control, in four of the ten single tone experiments, two frequencies were presented with equal probability as the shifted much less compared to the shifts observed following nearly simultaneous pairing of NB stimulation and tonal stimuli. Mean bandwidth at 10 dB above threshold was increased by 20% compared to controls. Although this decrease in selectivity resulted in an increase in the percent of cortex that responded to the paired stimulus, this increase was not selective for the paired frequency (Table 2). Thus, a delay between NB stimulation and auditory stimulation degraded the magnitude and selectivity of the NB-induced reorganization.

NB Stimulation Paired with Two Tone Frequencies

In five animals, two different tone frequencies were randomly interleaved and each paired with NB stimulation (4&14 or 9&19 kHz). In three animals, tuning curves appeared to shift preferentially toward one of the two paired frequencies. In the other two animals, many tuning curves appeared to have shifted such that their BF's were ultimately centered between the two paired frequencies. Pairing with two frequencies significantly increased the selectivity of frequency tuning. Mean bandwidth was decreased to 75% of control values (p<0.0001). A1 area was not significantly different from naive controls. The mean percent responding to each of the paired frequencies was not significantly different from controls.

NB Stimulation Paired with Modulated Auditory Stimuli

Pairing a train of six 9 kHz tones presented at 15 pps with NB stimulation resulted in a much larger effect on bandwidth compared to an unmodulated tone paired with NB stimulation. The average bandwidth at 10 dB above threshold was almost 60% greater than naive controls. Single units were sorted to demonstrate that this broadening was due to decreased frequency selectivity of individual neurons rather than increased variability of frequency preference of the units recorded at each site (mean single unit BW10: 1.38 versus 0.91, p<0.005). This significant decrease in frequency selectivity led to a plasticity effect that was less selective for 9 kHz compared to the unmodulated tone pairing. Most of the tuning curve shifts towards 9 kHz occurred as a result of increases in the preferred frequencies of previously low frequency neurons. The combination of wide tuning curves with significant BF shifts resulted in a very high percent of cortex responding to a 50 dB 9 kHz tone (72% compared to 43% for unmodulated 9 kHz [p<0.005] and 32% for controls [p<0.0001]). The mean surface area of A1 was also significantly increased compared to controls, resulting in a more than three-fold increase in the number of neurons responding to the paired frequency.

To examine the time course of NB-facilitated plasticity, two animals were mapped after only one week of pairing, instead of the month of pairing delivered in all of the other experiments in this study. The tuning curve shift toward 9 kHz were somewhat less than was observed after a month of pairing with the 9 kHz 15 pps train, but were comparable to the shifts observed after a month of pairing with an unmodulated 9 kHz tone. One week of pairing increased the percent of cortex responding to a 50 dB 9 kHz tone to 51% (p<0.05, compared to controls). Interestingly, the mean bandwidth at 10 dB above threshold was only increased by about 13%. Thus, most of the increase resulted from tuning curve shifts, not tuning curve widening. A1 area was not affected (2.0±0.3 mm$^2$).

In ten animals, stimuli with both temporal modulation and spectral variability were paired with NB activation. Tone frequency was selected randomly from seven possibilities, but was constant within each train. Each animal heard tones at only one repetition rate (5, 7.5, or 15 pps). Pairing multiple frequencies with NB stimulation had no systematic effect on the organization of the A1 frequency map. The area of A1 was not increased by NB pairing with trains of multiple frequencies. The plasticity of frequency selectivity tuning was significantly influenced by the repetition rate of the train paired with NB stimulation. Bandwidth was increased by 16, 27 and 35% after pairing with 5, 7.5 and 15 pps trains of multiple frequencies. The decrease in spectral selectivity resulting from pairing multi-frequency 15 pps trains was significantly less than resulted from pairing 15 pps trains with a constant 9 kHz carrier frequency (p<0.0005). Thus, plasticity of tuning curve bandwidth induced by NB stimulation was dependent on both spectral variability and temporal modulation of the paired auditory stimuli.

Plasticity of Other Response Characteristics

Minimum response latency was increased by three of the seven classes of stimuli paired with NB stimulation. The mean minimum neural response latency for naive animals was 15.1±0.2 msec. Pairing NB stimulation with two frequencies or with multiple frequencies modulated at 5 or 7 pps increased latencies to 16.4±0.3, 16.2±0.3, and 16.6±0.4 msec, respectively (p<0.0005). These three classes all had variable tone frequencies and slow modulation rates. NB stimulation paired with stimuli with either a rapid modulation rate or invariant carrier frequency did not significantly alter the minimum response latency (15.0±0.3, 14.8±0.3, 15.0±0.2 msec for single, 9 kHz train at 15 pps, and multiple frequency 15 pps train, respectively).

The mean number of spikes evoked per tone was statistically different from controls after pairing NB stimulation with trains of 9 kHz tones presented at 15 pps (2.1±0.1 versus 3.6±0.9; mean±standard error, p<0.05), but not after pairing any of the other stimulus sets used in this study. Evoked response to tonal stimuli was also increased when NB stimulation was separated from the auditory stimuli by ten seconds (2.1±0.1 versus 3.0±0.4; mean±standard error, p<0.05). Previous studies using cholinergic modulation observed highly specific changes in the number of spikes evoked by different tones within a neuron's receptive field. In some cases the neural response to frequencies within one-fourth of an octave were facilitated, while the responses to other nearby frequencies were inhibited [Balin, J. S., and N. M. Weinberger. *Proc Natl Acad Sci USA* 93: 11219–24 (1996); McKenna, T. M., J. H. Ashe, and N. M. Weinberger. *Synapse* 4: 30–43 (1989); Metherate, R., and N. M. Weinberger. *Brain Res* 480: 372–7 (1989); Metherate, R., and N. M. Weinberger. *Synapse* 6: 133–45 (1990)]. Most of the analysis in this study is focused on the receptive field as a unit and would not pick up changes in the response strength to frequencies within the tuning curve. To determine if such precise effects resulted from our long-term pairing of NB activation with tonal stimuli, the number of spikes evoked as a function of frequency was also examined for every tuning curve. We observed no consistent peak at the paired frequency in individual sites or in the population as a whole (data not shown). Minimum stimulus thresholds showed no consistent change as a result of pairing NB stimulation with any of the auditory stimuli used in this study.

Discussion:

Merzenich and colleagues observed plasticity in auditory and somatosensory cortex that appeared to be highly dependent on the nature of behaviorally relevant stimuli delivered during extended operant training of owl monkeys [Jenkins, W. M., M. M. Merzenich, M. T. Ochs, T. Allard, and E. Guic-Robles. *J Neurophysiol* 63: 82–104 (1990); Recanzone, G. H., M. M. Merzenich, and H. R. Dinse. *Cereb Cortex* 2: 181–96 (1992a); Recanzone, G. H., M. M. Merzenich, W. M. Jenkins, K. A. Grajski, and H. R. Dinse. *J Neurophysiol* 67: 1031–56 (1992b)]. In this study we used electrical stimulation of NB to activate cortical plasticity mechanisms and varied the paired sensory stimuli to explore the relationship between the statistics of the sensory input and the class, direction, and magnitude of cortical reorganization. We observed that stimulus repetition rate and spectral variability systematically alter a number of cortical response parameters, including preferred frequency (BF), tuning curve width (frequency tuning bandwidth), size of A1, cortical excitability (spikes/tone), stimulus following rate, and minimum latency (Table 3).

TABLE 3

Auditory Stimulus Determines NB-Induced Plasticity

| Experiment Group | TC Shift | Bandwidth | A1 Area | Spikes/ Tone | Maximum Repetition Rate | Minimum Latency |
|---|---|---|---|---|---|---|
| One Freq | ++ | + | ++ | 0 | n.d. | 0 |
| One Freq (w/unpaired) | ++ | 0 | ++ | 0 | n.d. | 0 |
| Out of phase | + | + | 0 | + | n.d. | ++ |
| Two Freq | ++ | — | 0 | 0 | n.d. | 0 |
| Lesion | 0 | + | 0 | 0 | n.d. | 0 |
| 15 pps 9 kHz | +++ | +++ | + | ++ | 0 | 0 |
| 15 pps multi | 0 | ++ | 0 | 0 | +++ | 0 |
| 7.5 pps multi | 0 | + | 0 | 0 | — | ++ |
| 5 pps multi | 0 | + | 0 | 0 | — | ++ |

Table 3 shows a summary of experimental results. Pluses denote parameters that were increased by NB stimulation paired with a given stimulus class, minuses denote decreases, and a zero indicates no significant difference from naive controls. The number of symbols indicates the size of the response.

NB-Induced Cortical Map Reorganizations

Electrical activation of nucleus basalis paired with tonal stimuli was sufficient to generate significant reorganization of the A1 map of frequency. The preferred frequency of cortical neurons systematically shifted toward the paired frequency, such that the number of cortical neurons responding to the stimulus paired with NB stimulation was doubled. Our results indicate that the responses of tens of thousands of A1 neurons are altered by NB stimulation in these passively stimulated animals.

Although the NB-induced increase in the size of the cortical representation was quite reliable, the direction of the tuning curve shift appeared to be a "free parameter." In some cases, high BF neurons shifted lower. In others, low BF neurons shifted higher. This variability was particularly clear when two different frequencies were paired with NB stimulation, in which case tuning curves either predominately shifted to one of the two frequencies, or to a point between them. Small differences in initial starting conditions due to individual experiences can have profound effects when competitive processes are involved, and may be responsible for this across-animal variability.

To demonstrate that cholinergic mechanisms are involved in this expansion, identical stimulation was delivered to rats with bilateral lesions of the cholinergic neurons that project from NB to the cortex. Consistent with previous reports that an intact NB is required for cortical map reorganization, no increase in the representation of the paired stimulus was observed [Baskerville, K. A., J. B. Schweitzer, and P. Herron. *Neuroscience* 80: 1159–69 (1997); Juliano, S. L., W. Ma, and D. Eslin. *Proc Natl Acad Sci USA* 88: 780–4 (1991); Sachdev, R. N., S. M. Lu, R. G. Wiley, and F. F. Ebner. *J Neurophysiol* 79: 3216–28 (1998); Webster, H. H., U. K. Hanisch, R. W. Dykes, and D. Biesold. *Somatosens Mot Res* 8: 327–46 (1991a); Zhu, X. O., and P. M. Waite. *Cereb Cortex* 8: 63–72 (1998)]. This result does not rule out the possibility that the electrical stimulation of the basal forebrain used in this study resulted in a global arousal state that was not specific to NB activity, and that no plasticity occurred as a non-specific effect of NB lesions. We do not favor this explanation, however, because there is no evidence that the NB stimulation used in this study were behaviorally arousing. The rats used in our experiments did not stop grooming, eating or sleeping when the basal forebrain was stimulated. Weinberger and colleagues also reported that similar stimulation produced no behavioral or autonomic responses [Bakin, J. S., and N. M. Weinberger. *Proc Natl Acad Sci USA* 93:11219–24 (1996)].

Using an acute preparation, Metherate and Ashe observed that short-term cortical plasticity was dependent on the relative timing of NB stimulation and cortical input [Metherate, R., and J. H. Ashe. *Brain Res* 559: 163–7 (1991); Metherate, R., and J. H. Ashe. *Synapse* 14: 132–43 (1993)]. Little or no plasticity was observed in those experiments if NB activity and stimulus were separated by more than a second. By delivering NB stimulation at three different times relative to tone onset, the importance of the timing of NB activity was confirmed. Plasticity was not obviously different when NB stimulation began either two hundred milliseconds before or fifty milliseconds after tone onset. When three different tones were presented but only one paired with NB stimulation, tuning curves shifted toward the paired frequency and not toward the frequencies that occurred as often, but were separated from NB stimulation by 8–30 seconds. When only one frequency was presented, the observed BF reorganization was decreased by the introduction of a ten-second delay between NB stimulation and tone onset. Thus, our results support previous observations that the effect of NB stimulation on cortical plasticity lasts at least a few hundred milliseconds, but less than several seconds.

Surprisingly, NB stimulation was sufficient to increase the total area of functionally defined primary auditory cortex. The magnitude of this expansion was determined by the particular auditory stimulus paired with NB stimulation. It appeared that the expansion of functionally-defined A1 was dependent on the degree of spectral variability. The surface area of A1 was increased by fifty percent when only one frequency (modulated or unmodulated) was paired with NB stimulation, while pairing with two or seven different tone frequencies resulted in no significant increase. Merzenich and colleagues also observed that the absolute size of a cortical zone could be expanded following some types of behavioral training [Jenkins, W. M., M. M. Merzenich, M. T. Ochs, T. Allard, and E. Guic-Robles. *J Neurophysiol* 63: 82–104 (1990); Merzenich, M. M., G. H. Recanzone, W. M. Jenkins, and K. A. Grajski. *Cold Spring Harb Symp Quant Biol* 55: 873–87 (1990)].

NB-Induced Plasticity of Frequency Selectivity

Receptive field size was very sensitive to the auditory stimulus paired with NB activation. Frequency tuning bandwidth was increased by up to 60% or decreased by up to 25% simply by pairing different classes of tonal stimuli with identical NB stimulation. The seven classes of stimuli used in this study increased bandwidth as a function of both increased repetition rate and decreased spectral variability. Recanzone, Merzenich, and colleagues observed a similar relationship following operant training of monkeys. Cortical receptive field size were decreased by practicing tasks involving stimuli delivered to different locations on the receptor surface (cochlea or skin), and were increased by training on a task requiring detection of changes in the modulation rate of stimuli delivered to an invariant skin location [Jenkins, W. M., M. M. Merzenich, M. T. Ochs, T. Allard, and E. Guic-Robles. *J Neurophysiol* 63: 82–104 (1990); Recanzone, G. H., M. M. Merzenich, and H. R. Dinse. *Cereb Cortex* 2: 181–96 (1992a); Recanzone, 6. H., M. M. Merzenich, W. M. Jenkins, K. A. Grajski, and H. R. Dinse. *J Neurophysiol* 67: 1031–56 (1992b)]. Our results extend those observations by independently varying spectral (spatial) variability and repetition rate. The finding that the statistics of the sensory input paired with NB stimulation generates analogous differential receptive field plasticity without behavioral training indicates that simple rules operate in the cortex to generate "usefuil" changes in circuitry based on the statistics of sensory stimuli marked by NB activity.

Recanzone and colleagues observed that training-induced changes in receptive field size were consistent with the operation of Hebb-like synapses driven to change by temporally coherent inputs in a competitive cortical network. They argued that larger receptive fields are generated by the temporally synchronous mactivity in response to low-frequency (10–20 Hz) stimulation at an invariant location of the receptor surface, while decreased receptive fields resulted from asynchronous cortical activity in response to stimuli that move across or are applied at inconsistent receptor locations (skin or cochlea). By systematically varying both spectral variability (1, 2 or 7 frequencies) and repetition rate (1, 5, 7.5, and 15 pps), our study strengthens the argument that receptive field size is determined by the structure of temporal correlations evoked by input sources.

The observation that bandwidth plasticity was not specific to the paired frequency is also consistent with plasticity effects induced by behavioral training in monkeys. The expansion of somatosensory receptive fields following training on a task involving vibration of only one digit was observed on several neighboring digits as well. Receptive field plasticity was not necessarily limited to neurons engaged by the sensory stimulus, but could influence the tuning properties of neurons located up to a millimeter away.

NB stimulation has been shown to increase the number of stimulus evoked spikes [Bakin, J. S., and N. M. Weinberger. *Proc Natl Acad Sci USA* 93: 11219–24 (1996); Edeline, J. M., B. Hars, C. Maho, and E. Hennevin. Exp *Brain Res* 97: 373–86 (1994a); Edeline, J. M., C. Maho, B. Hars, and E. Hennevin. *Brain Res* 636: 333–7 (1994b); Tremblay, N., R. A. Warren, and R. W. Dykes. *J Neurophysiol* 64: 1212–22 (1990); Webster, H. H., D. D. Rasmusson, R. W. Dykes, R. Schliebs, W. Schober, G. Bruckner, and D. Biesold. *Brain Res* 545: 292–6 (1991b)]. In the present paradigm, this increase was sensitive to the features of the auditory stimulus paired with NB stimulation. Of the seven classes of stimuli paired with NB stimulation, only 15 pps trains of 9 kHz tones resulted in a significant increase in evoked response strength (spikes/tone). Recanzone and colleagues also observed an increase in evoked responses after training monkeys on a task that involved the analogous tactile stimulus (a 20 Hz vibration of a single digit segment). Thus, our findings are consistent with previous demonstrations that response strength plasticity is strongly dependent on particular features of sensory inputs.

The maximum following rates of A1 neurons were decreased or increased by pairing NB stimulation with 5 or 15 pps tone trains, respectively [Kilgard, M. P., and M. M. Merzenich. *Nat Neurosci* 1: 727–731 (1998b)]. In agreement with the documented correlation between following rate and minimum response latency, we observed that latency was significantly increased following pairing with 5 or 7.5 pps multiple frequency tone trains [Brosch, M., and C. E. Schreiner. *J Neurophysiol* 77: 923–43 (1997); Kilgard, M. P., and M. M. Merzenich. *Nat Neurosci* 1: 727–731 (1998b); Raggio, M. W., and C. E. Schreiner. *J Neurophysiol* 72: 2334–59 (1994); Schreiner, C. E., J. Mendelson, M. W. Raggio, M. Brosch, and K. Krueger. *Acta Otolaryngol Suppl (Stockh)* 532: 54–60 (1997)].

Although several studies have reported that the cortical plasticity induced by a single episode of NB stimulation decays rapidly, other studies have observed longer lasting effects [Bjordahl, T. S., M. A. Dimyan, and N. M. Weinberger. *Behav Neurosci* 112: 467–479 (1998); Dykes, R., R. Metherate, and N. Tremblay. *J Neurophysiol* 63: 223 (1990); Edeline, J. M., B. Hars, C. Maho, and E. Hennevin. *Exp Brain Res* 97: 373–86 (1994a); Hars, B., C. Maho, J. M. Edeline, and E. Hennevin. *Neuroscience* 56: 61–74 (1993); Rasmusson, D. D., and R. W. Dykes. *Exp Brain Res* 70: 276–86 (1988); Tremblay, N., R. A. Warren, and R. W. Dykes. *J Neurophysiol* 64: 1212–22 (1990); Webster, H. H., D. D. Rasmusson, R. W. Dykes, R. Schliebs, W. Schober, G. Bruckner, and D. Biesold. *Brain Res* 545: 292–6 (1991b)]. All of the data presented in this study was collected from twenty-four to forty-eight hours after the last electrical activation of NB. The duration and size of the plasticity effects generated by repeated activation of NB suggest that short-lived NB-induced plasticity can become long-lasting with extended repetition over the course of days to weeks.

Behavioral Relevance

Nucleus basalis neurons respond vigorously to behaviorally important stimuli, either aversive or rewarding. The data set forth herein are consistent with the hypothesis that an important function of this activity is to mark individual events as behaviorally relevant so that cortical plasticity mechanisms can improve the representations of important stimuli [Ahissar, E., and M. Ahissar. *Curr Opin Neurobiol* 4: 580–7 (1994); Richardson, R. T., and M. R. DeLong. *Adv Exp Med Biol* 295: 233–52 (1991); Singer, W. *Eur Arch Psychiatry Neurol Sci* 236: 4–9 (1986); Weinberger, N. M. *Curr Opin Neurobiol* 3: 570–7 (1993)]. The temporal precision of NB-induced plasticity would prevent frequent and irrelevant stimuli from interfering with the learning of novel, relevant stimuli. This function is analogous to supervised neural network models used in a variety of applications (i.e., back-propagation), with the exception that this hypothesized "teacher" only provides information about which stimuli are important, not about how to alter connection weights and network dynamics to improve the quality of the sensory representation.

Although it seems obvious that the representation of a pure tone would be improved by increasing the number of neurons tuned for the tone's frequency, in fact the "ideal solution" depends entirely on what information is needed from the stimulus. If an animal is conditioned that a tonal stimulus predicts footshock, there is no way for it to know which features of the stimulus will predict shock in the future (duration, rise time, bandwidth, intensity, frequency, modulation rate, etc.). The fact that animals generalize indicates that they do not assume that all of the features are required. Evolution appears to have shaped brain circuitry such that its default guesses are appropriate based on the evolutionary history of the species (i.e., phyletic memory, see [Edelman, G. M. *Neural Darwinism: the theory of neuronal group selection.* New York: Basic Books (1987)]). These guesses may take the form of rules that operate within the brain to extract features of a stimulus that are most likely to contain relevant information based on other features of the stimulus and/or the context in which the stimulus appears.

Although the relationship between stimulus representation and information processing is far from understood, different behavioral tasks clearly result in different types of representational plasticity in the cortex [Jenkins, W. M., M. M. Merzenich, M. T. Ochs, T. Allard, and E. Guic-Robles. *J Neurophysiol* 63: 82–104 (1990); Recanzone, G. H., M. M. Merzenich, and H. R. Dinse. *Cereb Cortex* 2: 181–96 (1992a); Recanzone, G. H., M. M. Merzenich, W. M. Jenkins, K. A. Grajski, and H. R. Dinse. *J Neurophysiol* 67: 1031–56 (1992b)]. The cortical reorganizations observed in this study closely parallel the reorganizations that result from extended behavioral training. The similarity suggests that the sensory input itself can provide much of the information about how to improve sensory representations. In this initial study we focused on two stimulus features, repetition rate and spectral variability, and observed that each effected cortical plasticity in a systematic manner. These results indicate that the cortex uses these features to guide several forms of cortical plasticity, including reorganization of feature maps, plasticity of feature selectivity, expansion of a primary sensory cortical field, and increased strength of evoked responses. Additional experiments are needed to determine how other stimulus parameters shape representational plasticity.

In accordance with the present invention, the results of the research described above can be applied to humans. For example, the same techniques now used to treat Parkinson's disease by direct electrical stimulation in the basal ganglia can be adapted to stimulate the nucleus basalis and, thereby stimulate the release of acetylcholine to improve brain plasticity. The electrical stimulation of the nucleus basalis will coincide with the an important-to-remember stimulus or movement. This treatment can serve to overcome motivational problems in the early epoch of stroke recovery. The electrical stimuli of the nucleus basalis is expected to stimulate the release of acetylcholine, which magnifies and accelerates plasticity changes related to learning progressions in the brain. These changes are expected to closely parallel those progressions recorded in skill learning, with especially large and rapid changes. Moreover, these results are expected with a non-attending brain (i.e., without requiring the learning to pay close attention to the incoming stimuli). In addition, these changes are expected to be similar to those thought to occur during successful recovery from brain injury.

Because the release of acetylcholine is believed to be an important factor in this treatment, alternative embodiments can be implemented that delivery acetylcholine into the brain during the learning process. For example, microinjection, implanted micro release devices or implanted photo-sensitive release devices may be used to release acetylcholine into the brain to aid the learning process.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of stimulating brain plasticity in a subject comprising:

electrically stimulating the subject's nucleus basalis from 300 to 500 times per day with biphasic electrical pulses; and providing information to be learned to the subject substantially coincident with each electrical pulse.

2. The method of claim 1, wherein the subject's nucleus basalis is electrically stimulated from 300 to 400 times per day.

3. The method of claim 1, wherein the subject's nucleus basalis is electrically stimulated on each successive day for a plurality of days.

4. The method of claim 1, wherein the subject's nucleus basalis is electrically stimulated on each successive day for a period of from 20 days to 25 days.

5. The method of claim 1, wherein each of said biphasic electrical pulses has a current in the range of from 70 microamps to 150 microamps.

6. The method of claim 2, wherein the subject's nucleus basalis is electrically stimulated on each successive day for a plurality of days.

7. The method of claim 2, wherein the subject's nucleus basalis is electrically stimulated on each successive day for a period of from 20 days to 25 days.

8. The method of claim 2, wherein each of said biphasic electrical pulses has a currert in the range of from 70 microamps to 150 microamps.

* * * * *